(12) United States Patent
Shi et al.

(10) Patent No.: US 11,735,316 B2
(45) Date of Patent: Aug. 22, 2023

(54) METHOD AND APPARATUS OF LABELING TARGET IN IMAGE, AND COMPUTER RECORDING MEDIUM

(71) Applicants: Beijing BOE Technology Development Co., Ltd., Beijing (CN); BOE TECHNOLOGY GROUP CO., LTD., Beijing (CN)

(72) Inventors: Yongming Shi, Beijing (CN); Ge Ou, Beijing (CN); Qiong Wu, Beijing (CN); Chun Wang, Beijing (CN)

(73) Assignees: BEIJING BOE TECHNOLOGY DEVELOPMENT CO., LTD., Beijing (CN); BOE TECHNOLOGY GROUP CO., LTD., Beijing (CN)

( * ) Notice: Subject to any disclaimer, the term of this patent is extended or adjusted under 35 U.S.C. 154(b) by 357 days.

(21) Appl. No.: 17/253,216

(22) PCT Filed: Apr. 20, 2020

(86) PCT No.: PCT/CN2020/085613
§ 371 (c)(1),
(2) Date: Dec. 17, 2020

(87) PCT Pub. No.: WO2020/228490
PCT Pub. Date: Nov. 19, 2020

(65) Prior Publication Data
US 2021/0118137 A1   Apr. 22, 2021

(30) Foreign Application Priority Data
May 16, 2019   (CN) .......................... 201910406757.3

(51) Int. Cl.
*G06T 7/00*   (2017.01)
*G16H 30/40*   (2018.01)
(Continued)

(52) U.S. Cl.
CPC ........... *G16H 30/40* (2018.01); *G06F 18/214* (2023.01); *G06F 18/2431* (2023.01); *G06N 3/04* (2013.01);
(Continued)

(58) Field of Classification Search
CPC ........ G16H 30/40; G16H 30/20; G16H 50/20; G06F 18/214; G06F 18/2431; G06N 3/04;
(Continued)

(56) References Cited

U.S. PATENT DOCUMENTS 9,286,524 B1    3/2016  Mei et al.
2017/0213112 A1*  7/2017  Sachs ..................... G06N 3/045
(Continued)

FOREIGN PATENT DOCUMENTS

CN    106296699 A    1/2017
CN    107203781 A    9/2017
(Continued)

OTHER PUBLICATIONS

First Office Action, including Search Report, for Chinese Patent Application No. 201910406757.3, dated Dec. 10, 2020, 15 pages.
(Continued)

*Primary Examiner* — Van D Huynh
(74) *Attorney, Agent, or Firm* — Westman, Champlin & Koehler, P.A.

(57) ABSTRACT

The present disclosure provides a method and apparatus of labeling a target in an image, and a computer recording medium. The method includes: acquiring a first neural network, the first neural network includes a multi-layer convolutional neural network and a fully connected layer, wherein each layer of the multi-layer convolutional neural network includes a convolutional layer, an activation function layer and a down-sampling layer arranged successively; processing the image by using the multi-layer convolutional
(Continued)

neural network of the first neural network acquired so as to obtain a target position mask for the image; and labeling the target in the image based on the target position mask.

14 Claims, 6 Drawing Sheets

(51) Int. Cl.
*G06T 7/70* (2017.01)
*G06N 3/04* (2023.01)
*G06N 3/08* (2023.01)
*G06F 18/214* (2023.01)
*G06F 18/2431* (2023.01)
*G06V 10/764* (2022.01)
*G06V 10/82* (2022.01)
*G06V 10/44* (2022.01)

(52) U.S. Cl.
CPC ............. *G06N 3/08* (2013.01); *G06T 7/0012* (2013.01); *G06T 7/70* (2017.01); *G06V 10/454* (2022.01); *G06V 10/764* (2022.01); *G06V 10/82* (2022.01); *G06T 2207/20081* (2013.01); *G06T 2207/20084* (2013.01); *G06T 2207/30096* (2013.01)

(58) Field of Classification Search
CPC .......... G06N 3/08; G06N 3/045; G06N 3/088; G06T 7/0012; G06T 7/70; G06T 2207/20081; G06T 2207/20084; G06T 2207/30096; G06T 2207/10081; G06T 2207/10088; G06T 2207/10116; G06T 2207/10132; G06T 7/0014; G06V 10/454; G06V 10/764; G06V 10/82; G06V 2201/03
USPC .......................................................... 382/128
See application file for complete search history.

(56) References Cited

U.S. PATENT DOCUMENTS

| | | | |
|---|---|---|---|
| 2018/0260951 A1* | 9/2018 | Yang | G06N 3/084 |
| 2018/0365876 A1* | 12/2018 | Wimmer | G06T 11/60 |
| 2019/0035085 A1* | 1/2019 | Yu | G06T 7/174 |
| 2019/0370957 A1* | 12/2019 | Manickam | G06T 7/0012 |
| 2020/0058126 A1* | 2/2020 | Wang | G06F 18/213 |
| 2021/0118137 A1 | 4/2021 | Shi et al. | |

FOREIGN PATENT DOCUMENTS

| | | |
|---|---|---|
| CN | 108171232 A | 6/2018 |
| CN | 109087327 A | 12/2018 |
| CN | 110110808 A | 8/2019 |
| JP | 2010000180 A | 1/2010 |

OTHER PUBLICATIONS

"Remote sensing image aircraft target detection algorithm based on weakly supervised learning", dated Dec. 15, 2018, 18 pages.

* cited by examiner

METHOD AND APPARATUS OF LABELING TARGET IN IMAGE, AND COMPUTER RECORDING MEDIUM

CROSS REFERENCE TO RELATED APPLICATIONS

This application is a Section 371 National Stage Application of International Application No. PCT/CN2020/085613 filed on Apr. 20, 2020, entitled "METHOD AND APPARATUS OF LABELING TARGET IN IMAGE, AND COMPUTER RECORDING MEDIUM" which published as WO 2020/228490 AI on Nov. 19, 2020, not in English, and claims priority to Chinese Patent Application No. 201910406757.3 filed on May 16, 2019, the disclosures of which are incorporated herein by reference in their entireties;

TECHNICAL FIELD

The present disclosure relates to a field of image processing, and in particular to a method and apparatus of labeling a target in an image, and a computer recording medium.

BACKGROUND

Lesion position in a medical image needs to be determined by an experienced clinician, and the method of determining the lesion position based on algorithms of traditional feature detection or pattern recognition has a low accuracy. At present, although high-accuracy algorithms for automatically labeling the lesion position can be obtained by machine learning or deep learning, these algorithms need to be trained with the help of images in which lesion positions are labeled, which are difficult to acquire in practice.

SUMMARY

According to a first solution of the present disclosure, there is provided a method of labeling a target in an image, including: acquiring a first neural network, the first neural network includes a multi-layer convolutional neural network and a fully connected layer, wherein each layer of the multi-layer convolutional neural network includes a convolutional layer, an activation function layer and a down-sampling layer arranged successively; processing the image by using the multi-layer convolutional neural network of the first neural network acquired so as to obtain a target position mask for the image; and labeling the target in the image based on the target position mask.

In some embodiments, the processing the image by using the multi-layer convolutional neural network of the first neural network acquired so as to obtain a target position mask for the image includes:

performing a large-value spatial position sampling on an output of the activation function layer in at least one layer of the first neural network;

mapping an output of a down-sampling layer associated with the activation function layer to a coordinate space for the image based on a result of the large-value spatial position sampling, so as to obtain a mapping matrix; and obtaining the target position mask based on the mapping matrix.

In some embodiments, the output of the associated down-sampling layer is mapped to the coordinate space for the image via at least one layer of a de-convolutional neural network, and each layer of the de-convolutional neural network includes an up-sampling layer, an activation function layer and a de-convolutional layer arranged successively.

In some embodiments, the large-value spatial position sampling is performed for the output of the activation function layer in each layer of the first neural network, and the de-convolutional neural network is set corresponding to the convolutional neural network, and the mapping an output of the down-sampling layer associated with the activation function layer to a coordinate space for the image based on a result of the large-value spatial position sampling includes: mapping the output of the down-sampling layer in a last layer to the coordinate space for the image via the de-convolutional neural network, wherein the result of the large-value spatial position sampling for each layer of the convolutional neural network is used for directing an up-sampling for each layer of the de-convolutional neural network.

In some embodiments, an output of a de-convolutional layer in each layer of the de-convolutional neural network is used as an input of an up-sampling layer in a next layer of the de-convolutional neural network.

In some embodiments, the performing a large-value spatial position sampling on an output of the activation function layer in at least one layer of the first neural network includes: comparing the output of the activation function layer in the at least one layer with a first preset threshold; performing a binarization processing on a result of comparison; and recording spatial position information of a large-value element in a result of the binarization processing.

In some embodiments, the obtaining the target position mask based on the mapping matrix includes: comparing each element in the mapping matrix with a second preset threshold respectively; and performing a binarization processing on a result of comparison, so as to obtain the target position mask.

In some embodiments, the method further includes: training the first neural network by using a set of image samples in which disease classes are labeled.

In some embodiments, the target includes a lesion.

In some embodiments, a loss function used in the training is calculated based on an equation of $$L_i = -\log \frac{e^{f_i}}{\Sigma_j e^{f_j}}$$

where $f_i$ represents a score of an image with a disease class i being classified into i in response to being input into the first neural network, and $f_j$ represents a score of the image being classified into any disease class in response to being input into the first neural network.

In some embodiments, the training includes: updating each parameter in the first neural network based on the loss function and an equation of $$W = W - \alpha \frac{\partial L}{\partial W}$$

where L represents the loss function, W represents the parameter in the first neural network, and $\alpha$ represents an update rate.

In some embodiments, the labeling the target in the image based on the target position mask includes: labeling a pixel area in the image coordinated with a position with an intensity of 1 in the target position mask as a target area.

According to a second solution of the present disclosure, there is provided an apparatus of labeling a target in an image, including: a communication interface configured to receive the image; a memory on which computer executable instructions are stored; and a processor that, when executing the computer executable instructions, performs the method of labeling the target in the image according to the present disclosure.

According to a third solution of the present disclosure, there is provided a non-transitory computer recording medium on which computer executable instructions are stored, wherein the computer executable instructions when executed by a processor perform the steps of: acquiring a first neural network, the first neural network includes a multi-layer convolutional neural network and a fully connected layer, wherein each layer of the multi-layer convolutional neural network includes a convolutional layer, an activation function layer and a down-sampling layer arranged successively; processing the image by using the multi-layer convolutional neural network of the first neural network acquired so as to obtain a target position mask for the image; and labeling the target in the image based on the target position mask.

It should be understood that the foregoing general description and the following detailed description are only exemplary and illustrative, and are not intended to limit the present disclosure.

Summary of the present disclosure provides an overview of various implementations or examples of technologies described in the present disclosure, which is not a comprehensive disclosure of the full scope or all features of the disclosed technologies.

BRIEF DESCRIPTION OF THE DRAWINGS

In order to more clearly explain the technical solutions in the embodiments of the present disclosure, the drawings of the embodiments will be briefly introduced below. Obviously, the drawings in the following description are only some embodiments of the present disclosure, and are not intended to limit the present disclosure.

FIG. 4(*b*) is a schematic diagram of a specific embodiment of the method of labeling the target in the image according to the present disclosure;

FIG. 4(*c*) is a schematic diagram of a specific embodiment of the method of labeling the target in the image according to the present disclosure.

DETAILED DESCRIPTION

In order to make the purposes, technical solutions, and advantages of the present disclosure more clear, the technical solutions of the present disclosure are clearly and completely described below with reference to the drawings of the embodiments of the present disclosure. Obviously, the described embodiments are only a part but not all of the embodiments of the present disclosure. Based on the embodiments of the present disclosure, all other embodiments obtained by those ordinary skilled in the art without carrying out creative work fall within the protection scope of the present disclosure.

Unless otherwise defined, technical terms or scientific terms used in the present disclosure shall be of the general meaning understood by the ordinary skilled in the art. The words "comprising," "including" and the like indicate that the element or item preceding the word contains the elements or items listed following the word as well as the equivalents, but do not exclude other elements or items.

In order to keep the following description of the embodiments of the present disclosure clear and concise, detailed descriptions of known functions and known components are omitted in the present disclosure.

Figure 1:
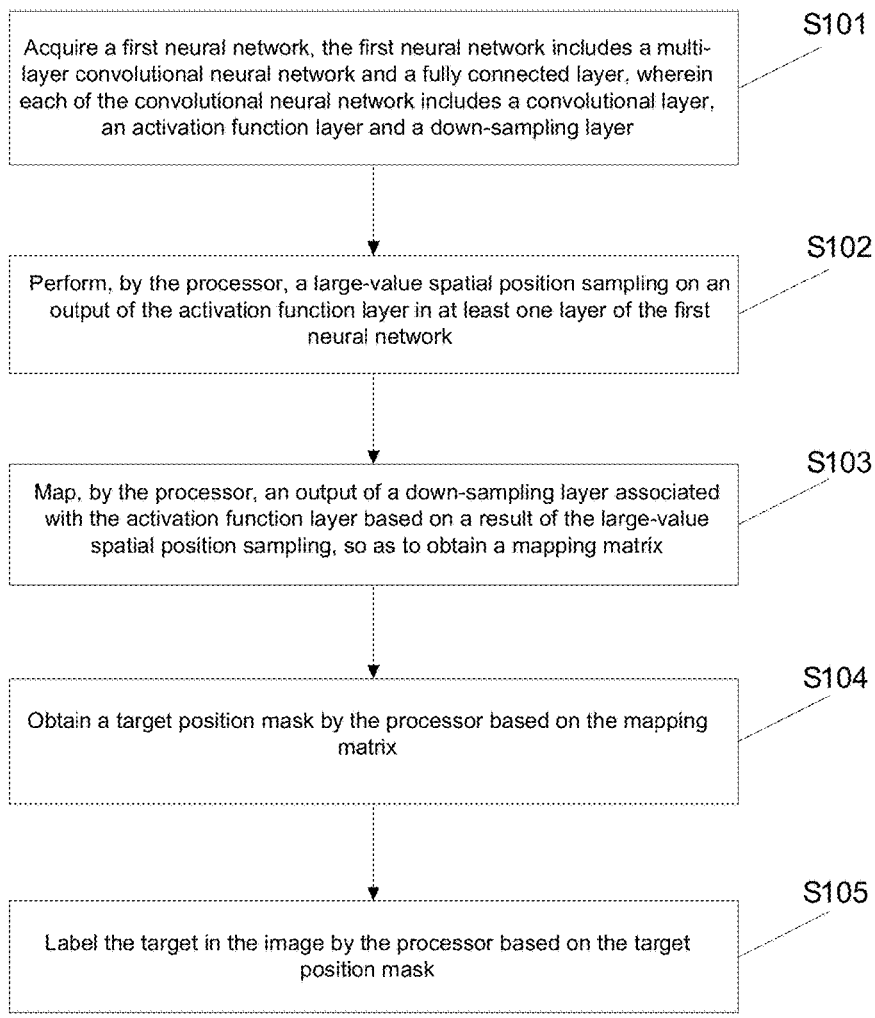
FIG. 1 is a flowchart of a method of labeling a target in an image according to an embodiment of the present disclosure.

The present disclosure provides a method and apparatus of labeling a target in an image and a computer recording medium, where a large-value spatial position sampling is performed on an output of an activation function layer in at least one layer of a first neural network trained for performing a target-related classification on the image, and an output of a down-sampling layer in an associated layer is mapped to the image based on a result of the large-value spatial position sampling, thereby obtaining a target position mask. This method achieves functions of a segmentation neural network by using the trained classification neural network, of which the training samples are easier to obtain and the training is easier. The method and apparatus conforming to the embodiments of the present disclosure are directly used to identify the target position in an image or a series of images, including a medical image or a series of medical images, such as tube radiography image, magnetic resonance image (MRI), computer tomography (CT) image, ultrasound image, etc. In the medical image, the target position may include a tumor position, an organ position, and so on. The image may be a 2D or 3D image. FIG. 1 is a flowchart of a method of labeling a target in an image according to an embodiment of the present disclosure. As shown in FIG. 1, the present disclosure provides a method of labeling a target in an image, including step S101 to step S105.

In step S101, a first neural network is acquired. The first neural network is a neural network model trained for performing a target-related classification on the image. The first neural network includes a multi-layer convolutional neural network and a fully connected layer. Each layer of the multi-layer convolutional neural network includes a convolutional layer, an activation function layer and a down-sampling layer arranged successively. Specifically, the convolutional layer, the activation function layer and the down-sampling layer successively form units of the convolutional neural network. Each layer of the multi-layer convolutional neural network may include a convolutional layer, an activation function layer and a down-sampling layer successively, and may also include a convolutional layer, an activation function layer, a convolutional layer, an activation function layer and a down-sampling layer, etc. successively, which are not specifically limited here. Specifically, the convolutional layer is used to extract features of the image, the activation function layer is used to activate the features extracted by the convolutional layer, and the down-sampling layer is used to reduce a dimensionality of the features and the amount of calculation. The fully connected layer is used to assign a corresponding weight to an output of the down-sampling layer. The down-sampling layer is for example but not limited to a pooling layer, such as a maximum pooling layer, an average pooling layer, and so on. By introducing the down-sampling layer, the field of view of learning may be expanded, thereby obtaining a more robust classification effect. In some embodiments, an activation function of the activation function layer may be a linear activation function or a nonlinear activation function. The first neural network for performing the target-related classification on the image may be obtained by training with a set of image samples in which disease classes are labeled. That is to say, in the training process, only the image samples in which disease classes are labeled are required, and image samples in which target (for example, lesion) positions are labeled are not required. The former is easier to obtain, which greatly reduces the difficulty of training.

Next, the image is processed by using the multi-layer convolutional neural network of the first neural network acquired so as to extract multi-level information of the image.

Specifically, in step S102, the large-value spatial position sampling is performed on the output of the activation function layer in at least one layer of the first neural network. In this way, the result of the large-value spatial position sampling includes spatial positions in the output of the activation function layer with intensities greater than a set threshold. These spatial positions with intensities greater than the set threshold may be recorded.

In step S103, an output of a down-sampling layer associated with the activation function layer in the at least one layer is mapped to a coordinate space for the image based on the result of the large-value spatial position sampling, so as to obtain a mapping matrix. Specifically, the associated down-sampling layer may be located in a certain layer or certain layers in the multi-layer convolutional neural network of the first neural network, such as the 10th layer, the last layer, the 1st to the 6th layers, etc. This layer may be the same as or different from the layer in which the large-value spatial position sampling is performed on the output of the activation function layer. For example, the output of the down-sampling layer in the 10th layer may be mapped to the coordinate space for the image based on the result of the large-value spatial position sampling for the activation function layer in the 10th layer, or based on the result of the large-value spatial position sampling for the activation function layer in the 6th layer, as long as one is mapped (for example but not limited to interpolation, pooling, etc.) to register with the other.

In step S104, the target position mask is obtained based on the mapping matrix obtained in step S103. Specifically, an element value in the mapping matrix is the intensity (for example, gray value) of a pixel of the image. The target position mask may be determined by processing the element value in the mapping matrix.

The method further includes, in step S105, labeling the target in the image based on the target position mask. Specifically, the target may be labeled in an input original image by comparing the target position mask with the original image.

According to the method of labeling the target in the image provided by the present disclosure, the large-value spatial position sampling is performed on the output of the activation function layer in at least one layer of the first neural network trained for performing the target-related classification on the image, and the output of the associated down-sampling layer is mapped to the image based on the result of the large-value spatial position sampling, thereby obtaining the target position mask. This method only trains the classification neural network and achieves the functions of the segmentation neural network by using the trained classification neural network, of which the training samples are easier to obtain and the training is easier.

In some embodiments, the output of the associated down-sampling layer is mapped to the coordinate space for the image via at least one layer of a de-convolutional neural network. Each layer of the de-convolutional neural network includes an up-sampling layer, an activation function layer and a de-convolutional layer arranged successively. Specifically, the up-sampling layer is used to amplify a size of the output image of the down-sampling layer in the associated layer of the convolutional neural network. The activation function of the activation function layer in this layer may be a nonlinear activation function or a linear activation function, which may be the same as or different from the activation function of the activation function layer in the convolutional neural network. The de-convolution layer is used to enrich the image content output by the activation function layer in this layer.

In some embodiments, the large-value spatial position sampling is performed for the output of each activation function layer in the first neural network, and the de-convolutional neural network is set corresponding to the convolutional neural network. The mapping the output of the down-sampling layer in the associated layer to the coordinate space for the image based on the result of the large-value spatial position sampling includes: mapping the output of the down-sampling layer in a last layer to the coordinate space for the image via the de-convolutional neural network, wherein the result of the large-value spatial position sampling for each layer of the convolutional neural network is used for directing an up-sampling for each layer of the de-convolutional neural network. Specifically, the large-value spatial position sampling is performed on the activation function layer in each layer of the first neural network. Starting from the last layer, based on the result of the large-value spatial position sampling for each layer, the output of the down-sampling layer in the associated layer is sequentially mapped to the coordinate space for the image until the result of the large-value space position sampling for the 1st layer of the convolutional neural network is mapped to the coordinate space for the image.

In some embodiments, the output of the de-convolutional layer in each layer of the de-convolutional neural network is used as an input of the up-sampling layer in a next layer of the de-convolutional neural network, so that multi-level information of the image is mapped to the image.

Figure 2:
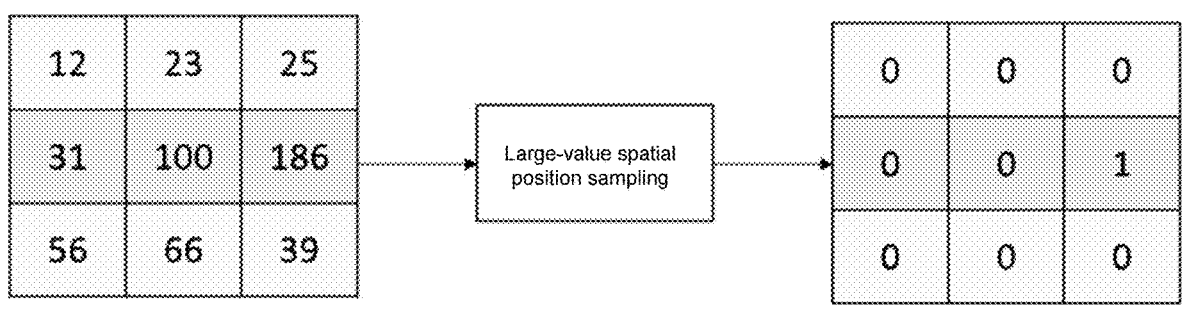
FIG. 2 is a diagram showing a comparison of before and after performing a large-value spatial position sampling on an output of an activation function layer of a convolutional neural network according to an embodiment of the present disclosure.

In some embodiments, the performing the large-value spatial position sampling on the output of the activation function layer in at least one layer of the first neural network includes: comparing the output of the activation function layer in the at least one layer with a first preset threshold; performing a binarization processing on a result of comparison; recording spatial position information of a large-value element in a result of the binarization processing. Specifically, the large-value spatial position sampling may be performed on the output of the activation function layer in a certain layer of the convolutional neural network, or the large-value spatial position sampling may be performed on the output of the activation function layer in each layer of the convolutional neural network. FIG. 2 is a diagram showing a comparison of before and after performing the large-value spatial position sampling on the output of the activation function layer in the convolutional neural network according to an embodiment of the present disclosure. As shown in FIG. 2, for example, the first preset threshold may be 120. The left part of the figure shows the output result of the activation function layer in a certain layer. Each element value in the output result is compared with the first preset threshold respectively. The intensity of the element greater than or equal to the first preset threshold is marked as 1, and the intensity of the element less than the first preset threshold is marked as 0. The result of performing the large-value spatial position sampling on the output result is shown in the right part of the figure.

In some embodiments, the obtaining the target position mask based on the mapping matrix includes: comparing each element in the mapping matrix with a second preset threshold respectively; and performing a binarization processing on a result of comparison, so as to obtain the target position mask. Specifically, the element value of the target position is different from the element values of other areas in the image. A user may determine the second preset threshold according to the actual situation. Each element value in the mapping matrix is compared with the second preset threshold respectively, and the binarization processing is performed on the result of comparison. The intensity of element greater than or equal to the second preset threshold is marked as 1, and the intensity of element less than the second preset threshold is marked as 0, so as to obtain the target position mask for the image.

In some embodiments, the method further includes: training the first neural network by using a set of image samples in which disease classes are labeled. Specifically, the set of image samples in which disease classes are labeled may be fracture images, tumor images, brain images, etc., which are not specifically limited here. The disease classes of image samples may be determined by an experienced clinician. Compared with the current method of using image samples in which lesion positions are labeled, the set of image samples in which disease classes are labeled is easier to obtain in practice, making the training of the first neural network easier.

In some embodiments, the target includes a lesion, such as a fracture site, a tumor site, etc. The large-value spatial position sampling is performed on the output of the activation function layer in at least one layer of the first neural network trained for performing a lesion-related classification on the image, and the output of the associated downsampling layer is mapped to the image based on the result of the large-value spatial position sampling, thereby obtaining the lesion position mask and labeling the lesion in the image.

In some embodiments, a loss function used in the training is calculated based on Equation (1) below:

$$L_i = -\log \frac{e^{f_i}}{\sum_j e^{f_j}} \qquad \text{Equation (1)}$$

where $f_i$ represents a score of an image with a disease class i being classified into i in response to being input into the first neural network, and $f_j$ represents a score of the image being classified into any disease class in response to being input into the first neural network. Specifically, the loss function corresponds to the classification method for classifying and selecting the output of the fully connected layer. The classification method may include, for example, support vector machine classification, softmax classification, etc., which are not specifically limited here.

In some embodiments, the training includes: updating each parameter in the first neural network based on the loss function and Equation (2) below:

$$W = W - \alpha \frac{\partial L}{\partial W} \qquad \text{Equation (2)}$$

where L represents the loss function, W represents the parameter in the first neural network, and $\alpha$ represents an update rate. The loss function is calculated according to the selected classification method, and the user may select the classification method and set the update rate according to the actual situation, so as to speed up the training of the first neural network.

In some embodiments, the labeling the target in the image based on the target position mask includes: labeling a pixel area in the image coordinated with a position with an intensity of 1 in the target position mask as a target area, and labeling a pixel area in the image coordinated with a position with an intensity of 0 in the target position mask as a non-target area. An AND operation may be performed on the target position mask and the input original image so as to label the target area in the image.

Specifically, the method of labeling the target in the image includes training the first neural network by using the set of image samples and labeling the target position of the image by using the first neural network trained for performing the target-related classification on the image.

Figure 3:
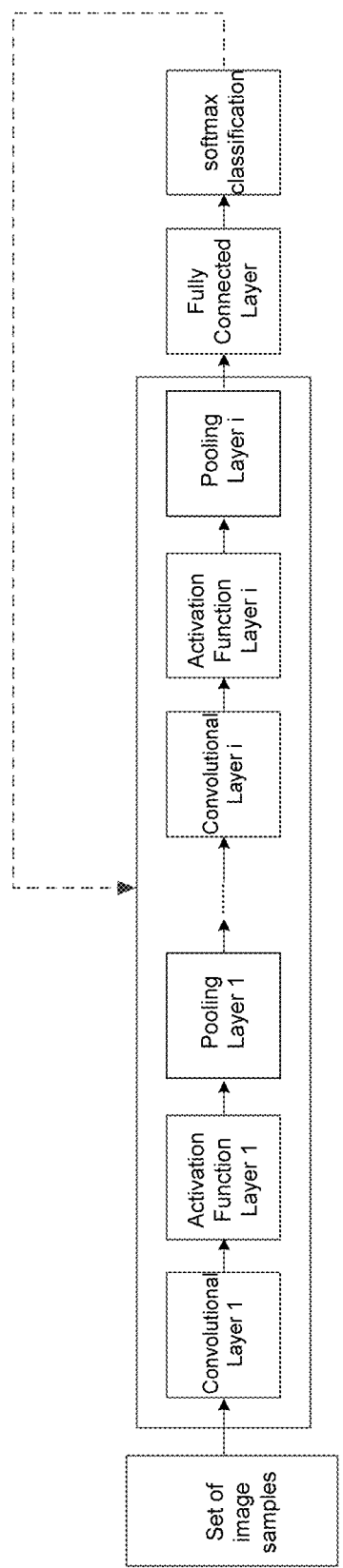
FIG. 3 is a schematic diagram of training a first neural network according to an embodiment of the present disclosure.

FIG. 3 is a schematic diagram of training the first neural network according to an embodiment of the present disclosure. As shown in FIG. 3, the set of image samples in which disease classes are labeled are first input into the first neural network. The multi-layer convolutional neural network of the first neural network may have a convolution kernel of 2×2, 5×5, etc., which is not specifically limited here. The activation function layer uses a non-linear activation function to activate image features extracted by the convolution layer. The fully connected layer gives a corresponding weight to the output of the pooling layer in the last layer of the convolutional neural network. Then the output result of the fully connected layer is classified by the softmax classification method. The loss function is calculated based on the classification result, and the parameters in the first neural network are updated based on the loss function obtained, as shown by the dotted line in FIG. 3.

Figure 4A:
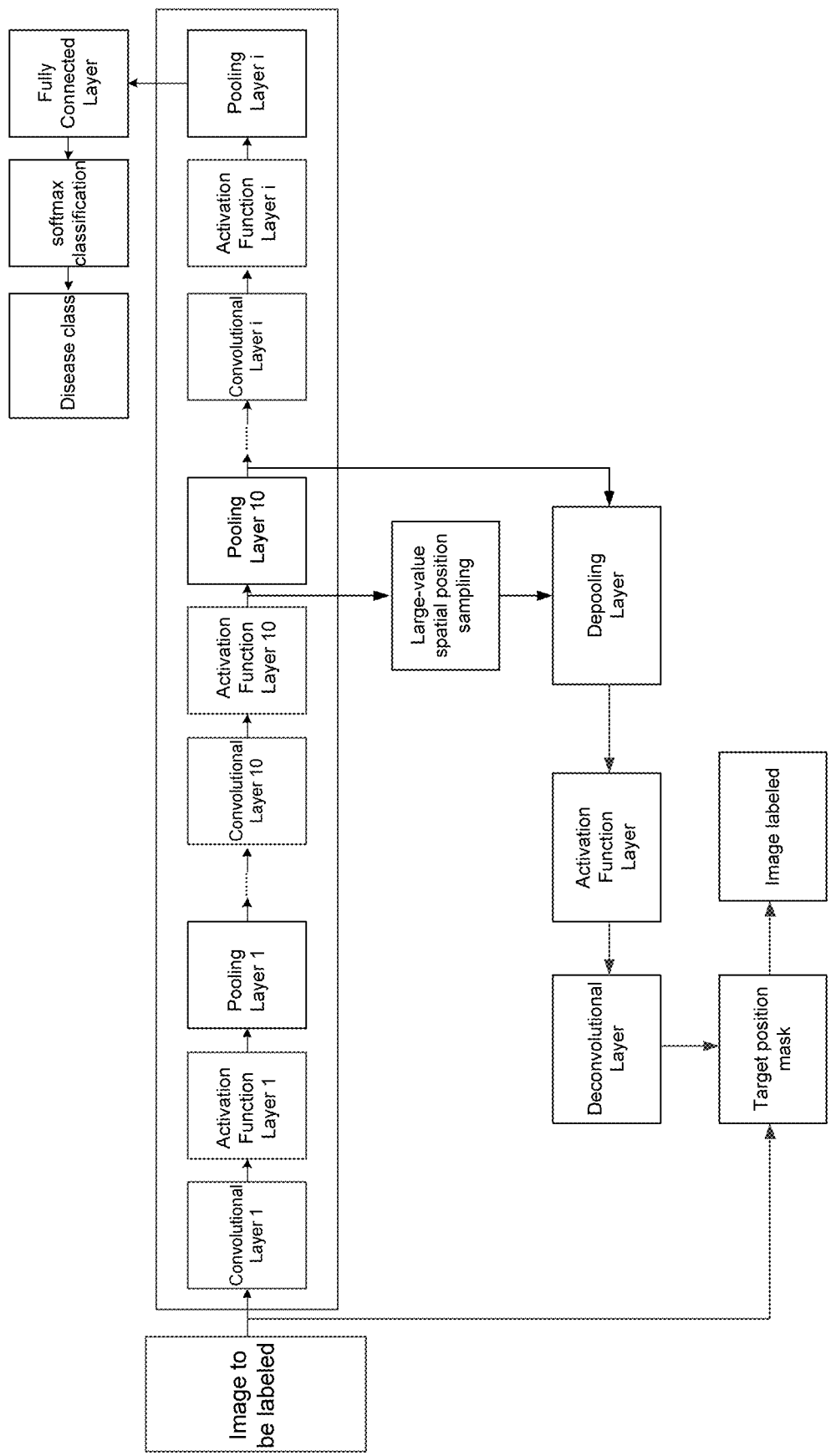
FIG. 4(*a*) is a schematic diagram of a specific embodiment of the method of labeling the target in the image according to the present disclosure.

FIG. 4(a) is a schematic diagram of a specific embodiment of the method of labeling the target in the image according to the present disclosure. As shown in FIG. 4(a), the image to be labeled is input into the first neural network trained for performing the target-related classification on the image obtained in FIG. 3, and the image is processed by the multi-layer convolutional neural network of the first neural network, then the first neural network outputs the disease class to which the image to be labeled belongs. In the process of processing the image by the multi-layer convolutional neural network, the large-value spatial position sampling is performed on the output of the activation function layer in a certain layer of the multi-layer convolutional neural network, for example, the 10th layer shown in FIG. 4(a). Next, the result of the large-value spatial position sampling for this layer together with the output of the pooling layer in this layer is input into at least one layer of the de-convolutional neural network, and then goes through the de-pooling layer, the activation function layer and the de-convolution layer successively. After that, the output of the de-convolution layer is processed to obtain the target position mask, and the image to be labeled is compared with the target position mask, thereby obtaining the image labeled. In some embodiments, the de-convolutional neural network may be set corresponding to the convolutional neural network so that they have the same number of layers and the same size of convolution/de-convolution kernel. The de-convolutional neural network may also be set non-corresponding to the convolutional neural network. For example, the de-convolutional neural network with fewer layers but larger kernel may be used for the convolutional neural network.

Figure 4B:
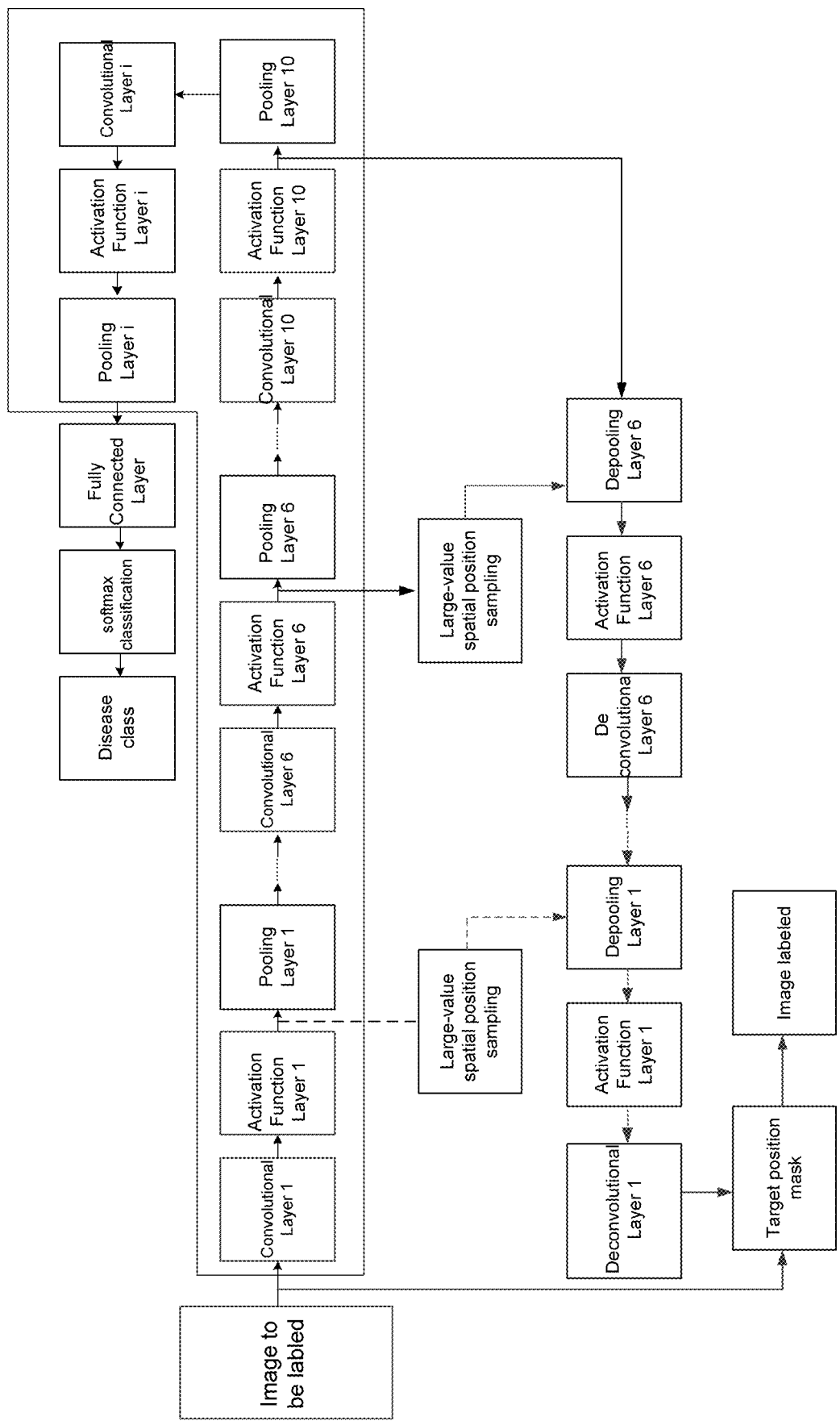

FIG. 4(b) is a schematic diagram of a specific embodiment of the method of labeling the target in the image according to the present disclosure. As shown in FIG. 4(b), the image to be labeled is input into the first neural network trained for performing the target-related classification on the image obtained in FIG. 3. In the process of processing the image by the multi-layer convolutional neural network of the first neural network, the large-value spatial position sampling may be performed on the output of the activation function layer in a certain layer or certain layers, for example, the 6th layer or the 1st to 6th layers shown in FIG. 4(b). Next, the result of the large-value spatial position sampling for each layer together with the output of the pooling layer in the layer in which the large-value spatial position sampling is not performed on the output of the activation function layer is input into the de-convolutional neural network. In some embodiments, the number of layers of the de-convolutional neural network may correspond to that of the convolutional neural network in which the large-value spatial position sampling is performed. The large-value spatial position sampling is performed on the output of the activation function layer in the ith layer (i is the sequence number of the layer which is a natural number) of the convolutional neural network, and the input of the de-pooling layer in the ith layer of the de-convolutional neural network is de-pooled based on the result of the large-value spatial position sampling. In this way, it does not need to make size adjustment and registration when the result of the large-value spatial position sampling is applied, which facilitates the process. After de-pooling, activation, and de-convolution are performed successively in the de-convolutional neural network, the output of the de-convolution layer is processed to obtain the target position mask, and the image to be labeled is compared with the target position mask, so as to obtain the image labeled.

Figure 4C:
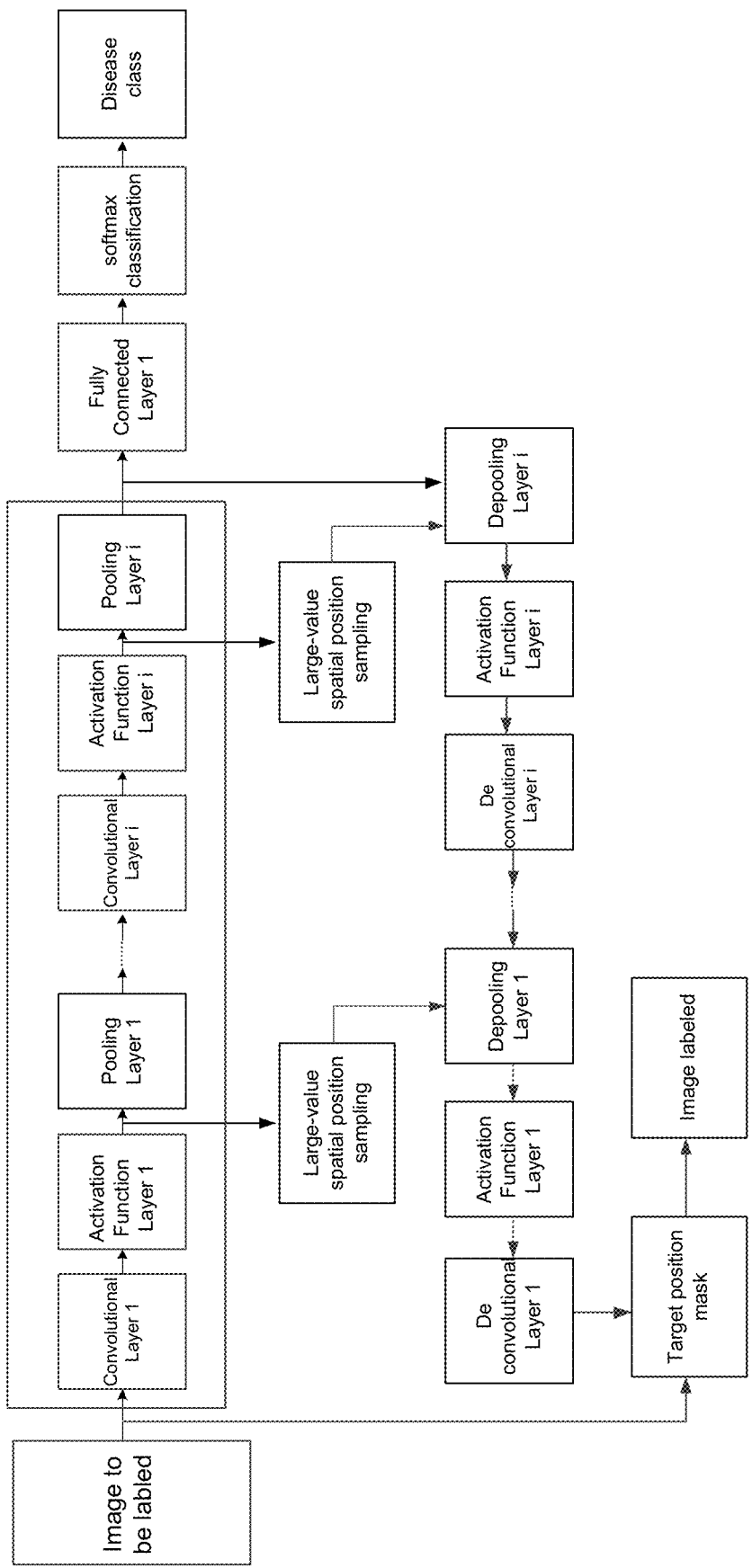

FIG. 4(c) is a schematic diagram of a specific embodiment of the method of labeling the target in the image according to the present disclosure. As shown in FIG. 4(c), the image to be labeled is input into the first neural network trained for performing the target-related classification on the image obtained in FIG. 3, where the de-convolutional neural network is set corresponding to the convolutional neural network. In the process of processing the image by the multi-layer convolutional neural network, the large-value spatial position sampling is performed on the output of the activation function layer in each layer. Next, the result of the large-value spatial position sampling for the last layer together with the output of the pooling layer in this layer is input into the corresponding de-convolutional neural network, and then goes through the de-pooling layer, the activation function layer and the de-convolution layer successively. After that, the output of the de-convolution layer and the result of the large-value spatial position sampling for the next layer are used as the input of the de-pooling layer in the next layer of the de-convolutional neural network, so that the de-pooling layer in the next layer of the de-convolutional neural network may perform de-pooling on the output of the de-convolutional layer in the previous layer based on the result of the large-value spatial position sampling for the next layer, and so on, until the first layer of the first neural network. After that, the output of the de-convolutional layer in the 1st layer is processed to obtain the target position mask, and the image to be labeled is compared with the target position mask, so as to obtain the image labeled.

Figure 5:
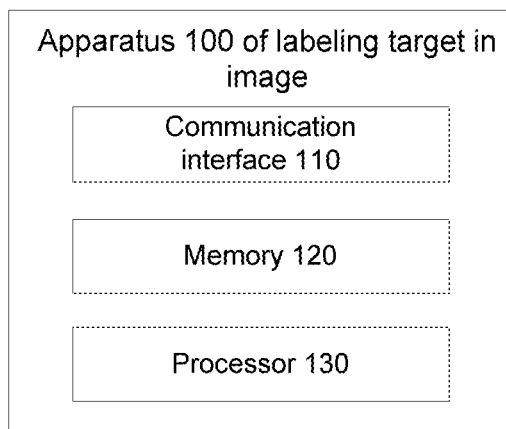
FIG. 5 is a schematic diagram of an apparatus of labeling a target in an image according to an embodiment of the present disclosure.

FIG. 5 is a schematic diagram of an apparatus 100 of labeling the target in the image according to an embodiment of the present disclosure. The apparatus 100 includes a communication interface 110, a memory 120, and a processor 130. The communication interface 110 is configured to receive the image, including the set of image sample for training the first neural network and the image to be labeled. The memory 120 stores computer-executable instructions. The processor 130, when executing the computer-executable instructions, performs the method of labeling the target in the image according to any embodiment of the present disclosure. Specifically, first, the communication interface 110 receives the set of image samples provided by the image database for training the first neural network. Then the processor 130 trains the first neural network by using the computer executable instructions stored in the memory 120 and the set of image samples received so as to obtain the first neural network trained for performing the target-related classification on the image. When the communication interface 110 receives the image to be labeled, the processor 130 inputs the image to the trained first neural network and processes the image, so as to obtain the target position mask for the image and label the target position in the image.

According to the apparatus 100 of labeling the target in the image provided by the present disclosure, the large-value spatial position sampling is performed on the output of the activation function layer in at least one layer of the first neural network trained for performing the target-related classification on the image, and the output of the associated down-sampling layer is mapped to the image based on the result of the large-value spatial position sampling, thereby obtaining the target position mask. The apparatus achieves the functions of the segmentation neural network by using the classification neural network, of which the training samples are easier to obtain, and the training is easier.

The present disclosure further provided a non-transitory computer recording medium on which computer executable instructions are stored, wherein the computer executable instructions when executed by a processor perform the steps of: acquiring the first neural network, the first neural network includes a multi-layer convolutional neural network and a fully connected layer, wherein each layer of the multi-layer convolutional neural network includes a convolutional layer, an activation function layer and a down-sampling layer arranged successively; processing the image by using the multi-layer convolutional neural network of the first neural network acquired so as to obtain the target position mask for the image; and labeling the target in the image based on the target position mask.

The present disclosure describes various operations or functions, which may be implemented as software codes or instructions or defined as software codes or instructions. Such content may be source code or differential code ("delta" or "patch" code) that may be directly executed (in "object" or "executable" form). The software implementation of the embodiments described herein may be provided by a product with codes or instructions stored thereon, or provided by a method of operating a communication interface to transmit data through the communication interface. A machine or computer-readable storage medium may cause a machine to perform the described functions or operations, and includes any mechanism that stores information in a form accessible by a machine (e.g., computing device, electronic system, etc.), such as recordable/non-recordable media (for example, read only memory (ROM), random access memory (RAM), magnetic disk storage media, optical storage media, flash memory devices, etc.). The communication interface includes any interface in hard-wired, wireless, optical and other media for communicating with other devices, such as a memory bus interface, a processor bus interface, an Internet connection, a disk controller, etc. The communication interface may be configured by providing configuration parameters and/or transmitting signals to prepare the communication interface so as to provide data signals describing software content. The communication interface may be accessed by sending one or more commands or signals to the communication interface.

The computer-executable instructions of the embodiments of the present disclosure may be organized into one or more computer-executable components or modules. Any number and combination of such components or modules may be used to implement various aspects of the present disclosure. For example, various aspects of the present disclosure are not limited to the specific computer-executable instructions or specific components or modules shown in the drawings and described herein. Other embodiments may include different computer-executable instructions or components with more or fewer functions than shown and described herein.

The above description is intended to be illustrative and not restrictive. For example, the above examples (or one or more of them) may be used in combination with each other. For example, those ordinary skilled in the art may use other embodiments when reading the foregoing description. In addition, in the above specific embodiments, various features may be grouped together to simplify the present disclosure. This should not be interpreted as an intent that a disclosed feature that is not claimed is necessary for any claim. On the contrary, the subject matter of the present disclosure may be less than all the features of a specific disclosed embodiment. Thus, the following claims are incorporated herein as examples or embodiments in the detailed description, wherein each claim independently serves as a separate embodiment, and it is considered that these embodiments may be combined with each other in various combinations or permutations. The scope of the present disclosure should be determined with reference to the appended claims and the full scope of equivalents entitled by these claims.

The above embodiments are only exemplary embodiments of the present disclosure, and are not used to limit the present disclosure, and the protection scope of the present disclosure is defined by the claims. Those skilled in the art may make various modifications or equivalent substitutions to the present disclosure within the essence and protection scope of the present disclosure, and such modifications or equivalent substitutions should also be regarded as falling within the protection scope of the present disclosure.

The invention claimed is:

1. A method of labeling a target in an image, comprising:
   acquiring an image;
   acquiring a first neural network, the first neural network comprises a multi-layer convolutional neural network and a fully connected layer, wherein each layer of the multi-layer convolutional neural network comprises a convolutional layer, an activation function layer and a down-sampling layer arranged successively;
   processing the image by using the multi-layer convolutional neural network of the first neural network acquired so as to obtain a target position mask for the image; and
   labeling the target in the image based on the target position mask,
   wherein the processing the image by using the multi-layer convolutional neural network of the first neural network acquired so as to obtain a target position mask for the image comprises:
   performing a large-value spatial position sampling on an output of the activation function layer in at least one layer of the first neural network;
   mapping an output of a down-sampling layer associated with the activation function layer to a coordinate space for the image based on a result of the large-value spatial position sampling, so as to obtain a mapping matrix; and
   obtaining the target position mask based on the mapping matrix.

2. The method of labeling the target in the image according to claim 1, wherein the output of the associated down-sampling layer is mapped to the coordinate space for the image via at least one layer of a de-convolutional neural network, and wherein each layer of the de-convolutional neural network comprises an up-sampling layer, an activation function layer and a de-convolutional layer arranged successively.

3. The method of labeling the target in the image according to claim 2, wherein the large-value spatial position sampling is performed for the output of the activation function layer in each layer of the first neural network, and the de-convolutional neural network is set for the convolutional neural network, and
   wherein the mapping an output of a down-sampling layer associated with the activation function layer to a coordinate space for the image based on a result of the large-value spatial position sampling comprises:
   mapping the output of the down-sampling layer in a last layer to the coordinate space for the image via the de-convolutional neural network, wherein the result of the large-value spatial position sampling for each layer of the convolutional neural network is used for directing an up-sampling for each layer of the de-convolutional neural network.

4. The method of labeling the target in the image according to claim 2, wherein an output of the de-convolutional layer in each layer of the de-convolutional neural network is used as an input of the up-sampling layer in a next layer of the de-convolutional neural network.

5. The method of labeling the target in the image according to claim 1, wherein an output of a de-convolutional layer in each layer of a de-convolutional neural network is used as an input of an up-sampling layer in a next layer of the de-convolutional neural network.

6. The method of labeling the target in the image according to claim 1, wherein the performing a large-value spatial position sampling on an output of the activation function layer in least one layer of the first neural network comprises:
   comparing the output of the activation function layer in the at least one layer with a first preset threshold;

performing a binarization processing on a result of comparison; and recording spatial position information of a large-value element in a result of the binarization processing.

7. The method of labeling the target in the image according to claim 1, wherein the obtaining the target position mask based on the mapping matrix comprises:

comparing each element in the mapping matrix with a second preset threshold respectively; and performing a binarization processing on a result of comparison, so as to obtain the target position mask.

8. The method of labeling the target in the image according to claim 1, further comprising: training the first neural network by using a set of image samples in which disease types are labeled.

9. The method of labeling the target in the image according to claim 1, wherein the target comprises a lesion.

10. The method of labeling the target in the image according to claim 9, wherein a loss function used in the training is calculated based on an equation of $$L_i = -\log\frac{e^{f_i}}{\Sigma_j e^{f_j}}$$

where fi represents a score of an image with a disease class i being classified into i in response to being input into the first neural network, and fj represents a score of the image being classified into any disease type in response to being input into the first neural network.

11. The method of labeling the target in the image according to claim 10, wherein the training comprises: updating each parameter in the first neural network based on the loss function and an equation of $$W = W - \alpha\frac{\partial L}{\partial W}$$

where L represents the loss function, W represents the parameter in the first neural network, and α represents an update rate.

12. The method of labeling the target in the image according to claim 1, wherein the labeling the target in the image based on the target position mask comprises:

labeling a pixel area in the image coordinated with a position with an intensity of 1 in the target position mask as a target area.

13. An apparatus of labeling a target in an image, comprising:

a communication interface configured to receive the image;

a memory on which computer executable instructions are stored; and a processor that, when executing the computer executable instructions, performs the method of labeling the target in the image according to claim 1.

14. A non-transitory computer recording medium on which computer executable instructions are stored, wherein the computer executable instructions when executed by a processor perform the steps of:

acquiring a first neural network, the first neural network comprises a multi-layer convolutional neural network and a fully connected layer, wherein each layer of the multi-layer convolutional neural network comprises a convolutional layer, an activation function layer and a down-sampling layer arranged successively;

processing the image by using the multi-layer convolutional neural network of the first neural network acquired so as to obtain a target position mask for the image; and labeling the target in the image based on the target position mask, wherein the processing the image by using the multi-layer convolutional neural network of the first neural network acquired so as to obtain a target position mask for the image comprises:

performing a large-value spatial position sampling on an output of the activation function layer in at least one layer of the first neural network;

mapping an output of a down-sampling layer associated with the activation function layer to a coordinate space for the image based on a result of the large-value spatial position sampling, so as to obtain a mapping matrix; and obtaining the target position mask based on the mapping matrix.

* * * * *